(12) United States Patent  (10) Patent No.: US 7,893,409 B1
Cousins  (45) Date of Patent: Feb. 22, 2011

(54) TRANSIENT PHOTOLUMINESCENCE MEASUREMENTS

(75) Inventor: Peter Cousins, Menlo Park, CA (US)

(73) Assignee: Sunpower Corporation, San Jose, CA (US)

( * ) Notice: Subject to any disclaimer, the term of this patent is extended or adjusted under 35 U.S.C. 154(b) by 78 days.

(21) Appl. No.: 12/154,616

(22) Filed: May 22, 2008

Related U.S. Application Data

(60) Provisional application No. 60/931,934, filed on May 25, 2007.

(51) Int. Cl.
*G01J 3/32* (2006.01)

(52) U.S. Cl. ............... 250/472.1; 250/483.1; 250/492.1; 250/492.2

(58) Field of Classification Search ... 250/458.1–461.2, 250/472.1–473.1, 483.1, 492.1–492.2; 356/317–318, 356/326
See application file for complete search history.

(56) References Cited

U.S. PATENT DOCUMENTS

| | | | | |
|---|---|---|---|---|
| 3,891,853 | A * | 6/1975 | Kremen et al. ............ | 250/458.1 |
| 5,585,639 | A * | 12/1996 | Dorsel et al. ............. | 250/458.1 |
| 5,974,860 | A * | 11/1999 | Kuroda et al. .................. | 73/40 |
| 6,534,774 | B2 * | 3/2003 | Hasegawa et al. ........ | 250/458.1 |
| 2001/0055114 | A1 * | 12/2001 | Suzuki et al. ............... | 356/317 |

FOREIGN PATENT DOCUMENTS

WO    WO 2007048108 A2 *   4/2007

OTHER PUBLICATIONS

Han et al. (2001), "A Direction Comparison Between Terahertz Time-Domain Spectroscopy and Far-Infrared Fourier Transform Spectroscopy," Journal of Applied Physics (89) 4: p. 2457-9.*
T. Trupke et al., "Fast Photoluminescence Imaging of Silicon Wafers", 2006 IEEE, pp. 928-931.
Gerard Marriott et al., "Time resolved imaging microscopy, Phosphorescence and delayed fluorescence imaging", Biophys. J. © Biophysical Society, vol. 60, Dec. 1991, pp. 1374-1387.

* cited by examiner

*Primary Examiner*—David P. Porta
*Assistant Examiner*—Casey Bryant
(74) *Attorney, Agent, or Firm*—Blakely, Sokoloff, Taylor & Zafman LLP

(57) ABSTRACT

A photoluminescence mapping system and method for use in fabricating solar cells that eliminates the need for complex and expensive light sources, filters and high sensitivity cameras. Generally, the method includes: (i) irradiating a surface of the substrate with radiation having a predetermined energy for a first predetermined period of time to photogenerate carriers therein; (ii) stopping the irradiation; (iii) exposing the surface of the substrate to a camera for a second predetermined period of time; and (iv) capturing with the camera a photoluminescence (PL) signal emitted from the surface of the substrate.

20 Claims, 4 Drawing Sheets

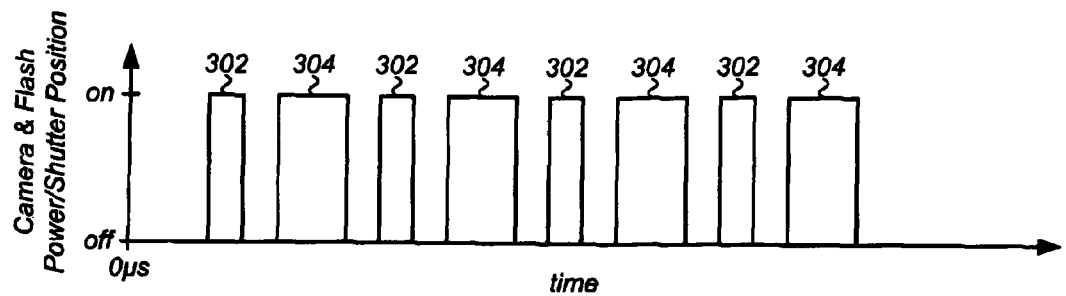
FIG. 3A
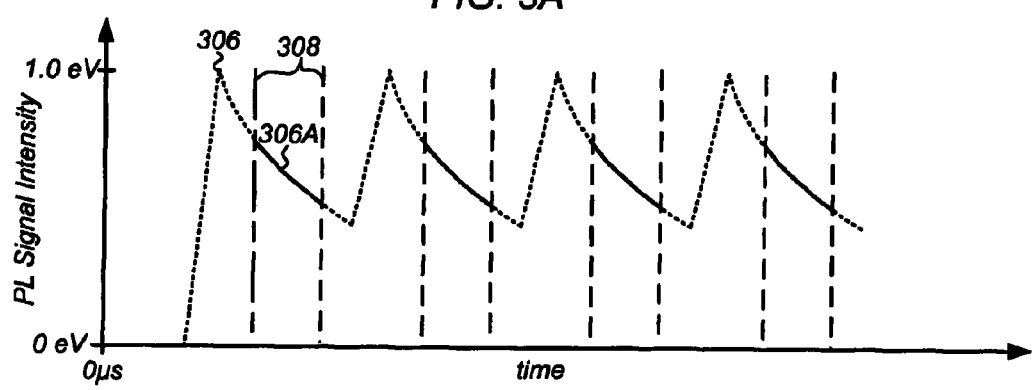
FIG. 3B
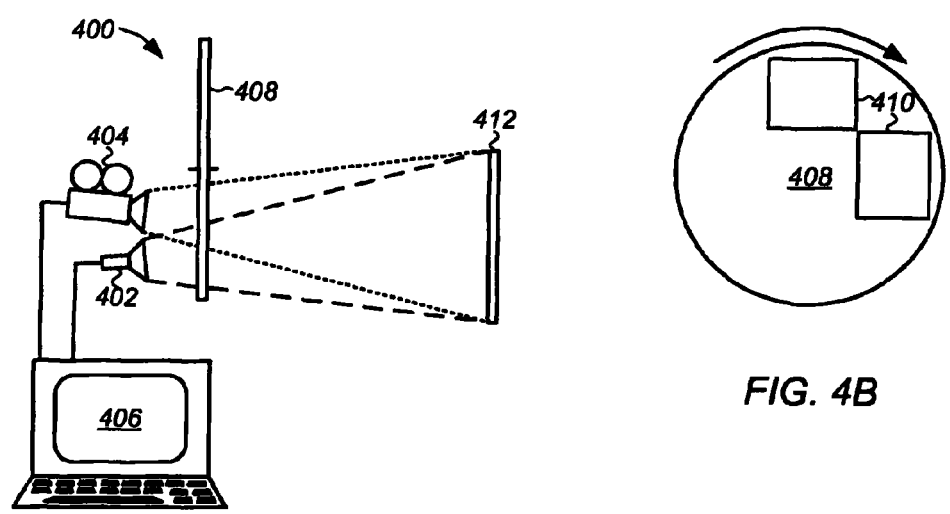
FIG. 4A
FIG. 4B

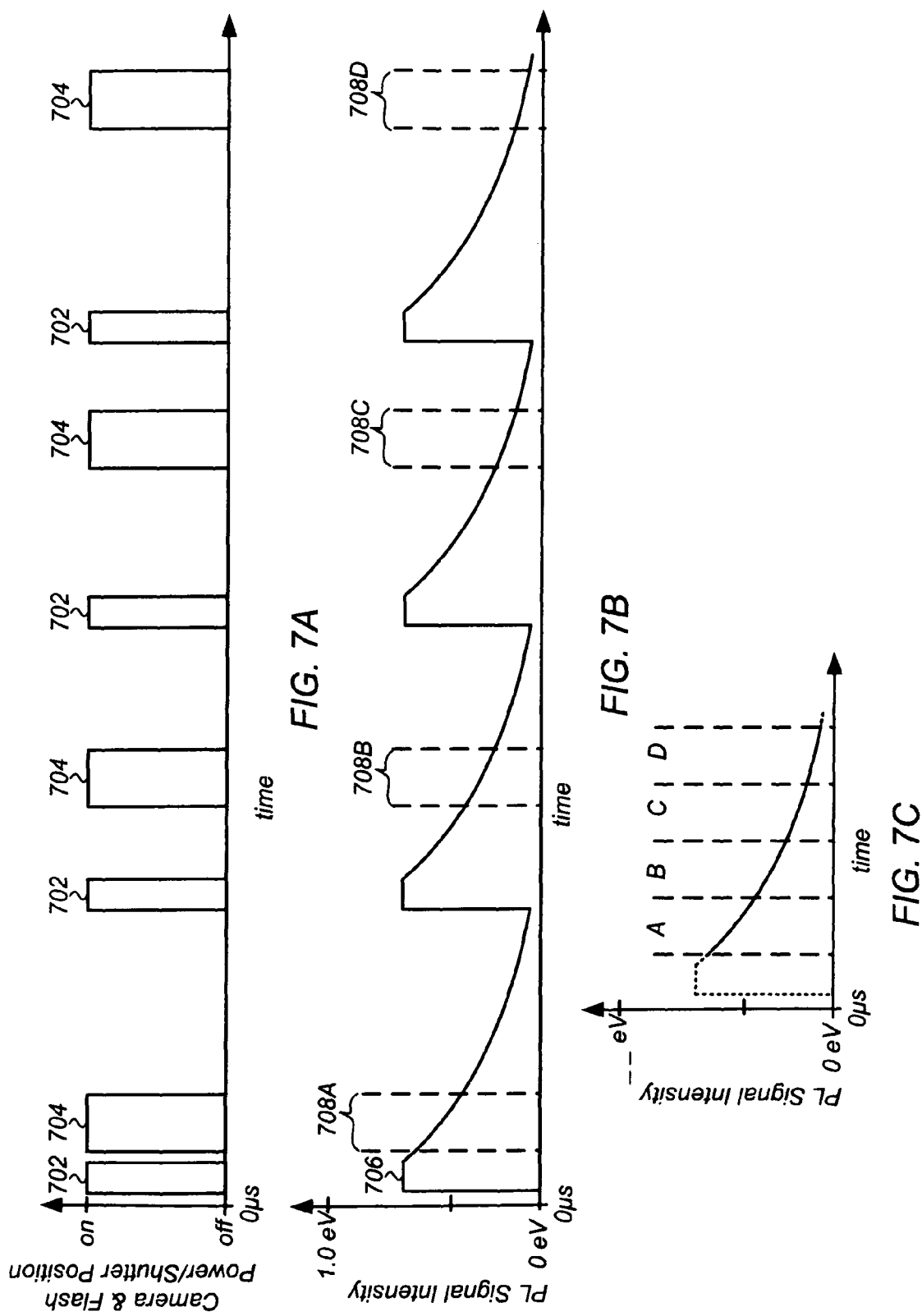

TRANSIENT PHOTOLUMINESCENCE MEASUREMENTS

REFERENCE TO RELATED APPLICATION

This application claims the benefit of U.S. Provisional Application No. 60/931,934 filed May 25, 2007, which is incorporated by reference herein.

TECHNICAL FIELD

Embodiments of the present invention relate generally to photo voltaic photovoltaic solar cells, and more particularly to an apparatus and methods for photoluminescence imaging of test wafers during a solar cell fabrication process.

BACKGROUND

Photo voltaic Photovoltaic cells, commonly known as solar cells, are well known devices for direct conversion of solar radiation into electrical energy.

Generally, solar cells are fabricated on a semiconductor wafer or substrate using semiconductor processing techniques to form a p-n junction near a surface of the substrate. Solar radiation impinging on the surface of the substrate creates charge carriers, electron and hole pairs, in the bulk of the substrate, which migrate to p-doped and n-doped regions in the substrate, thereby generating a voltage differential between the doped regions. The doped regions are coupled to metal contacts on the solar cell to direct an electrical current from the cell to an external circuit coupled thereto.

The efficiency of a solar cell in converting incident radiation or light into electrical energy is directly dependent on the photogeneration rate and the effective lifetime of the carriers within the semiconductor substrate. Consequently, it is generally desirable to measure or characterize these properties, photogeneration rate and effective carrier lifetime, for a wafer or substrate prior to fabrication of a solar cell or cells therein, and, using test wafers, at several points during the fabrication process.

One technique commonly used to measure photogeneration rate and effective carrier lifetime in silicon solar cells involves photoluminescence imaging or mapping of the wafer. Briefly, in photoluminescence imaging a steady-state coherent light source, such as a laser, having a particular wavelength (i.e. 800 nm) or a narrow range of wavelengths, is used to stimulate photogeneration of carriers within the wafer. The density of these carriers can then be estimated by monitoring their radiative recombination using a highly sensitive camera to capture the photoluminescence image. A complex and expensive filtering system is required in front of the camera to filter out the stimulation light.

Accordingly, there is a need for a simplified photoluminescence mapping system and method for use in fabricating solar cells that eliminate the need for complex and expensive light sources, filters and high sensitivity cameras.

BRIEF DESCRIPTION OF THE DRAWINGS

These and various other features and advantages of the present invention will be apparent upon reading of the following detailed description in conjunction with the accompanying drawings and the appended claims provided below, where:

FIG. 3A is a timing diagram illustrating exposure of substrate to a stimulation light source and the subsequent exposure of a camera to the resulting photoluminescence according to another embodiment of the present invention;

FIG. 3B is a graph illustrating a PL signal intensity over time following exposure of substrate to a stimulation light source of FIG. 3A;

FIG. 4 is a schematic block diagram of a system for measuring transient photoluminescence of a substrate having a low photoluminescence LT according to an embodiment of the present invention;

FIG. 7A is a timing diagram illustrating a method for determining decay of a photoluminescence signal according to another embodiment of the present invention;

FIG. 7B is a graph illustrating a PL signal intensity over time following exposure of substrate to a stimulation light source of FIG. 7A; and FIG. 7C is a graph illustrating decay of a PL signal intensity over time as determined from the graph of FIG. 7B.

DETAILED DESCRIPTION

The present invention is directed to a simplified photoluminescence mapping system and method for use in fabricating solar cells.

In the following description, for purposes of explanation, numerous specific details are set forth in order to provide a thorough understanding of the present invention. It will be evident, however, to one skilled in the art that the present invention may be practiced without these specific details. In other instances, well-known structures, and techniques are not shown in detail or are shown in block diagram form in order to avoid unnecessarily obscuring an understanding of this description.

Reference in the description to "one embodiment" or "an embodiment" means that a particular feature, structure, or characteristic described in connection with the embodiment is included in at least one embodiment of the invention. The appearances of the phrase "in one embodiment" in various places in the specification do not necessarily all refer to the same embodiment. The term "to couple" as used herein may include both to directly connect and to indirectly connect through one or more intervening components.

Systems and methods for characterizing or mapping transient photoluminescence of wafers or substrates according to certain embodiment of the present invention will now be described in detail with reference to FIGS. 1A-6.

Figure 1A:
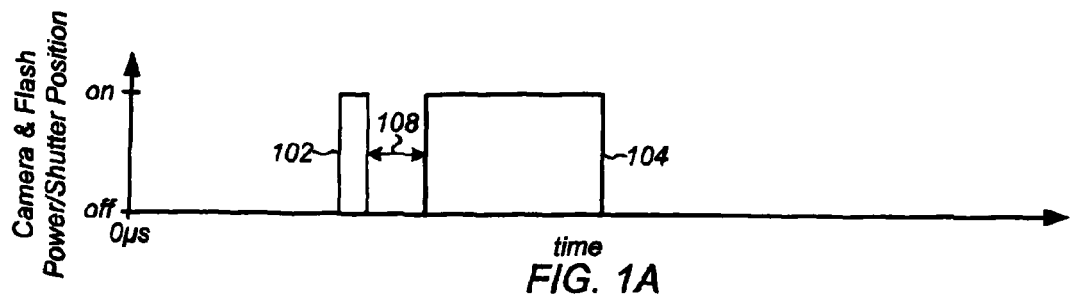
FIG. 1A is a timing diagram illustrating exposure of substrate to a stimulation light source and the subsequent exposure of a camera to the resulting photoluminescence according to an embodiment of the present invention.

Generally, the method involves irradiating a surface of a substrate with radiation or light having a predetermined energy for a first predetermined period of time, indicated by trace 102 in FIG. 1A, followed by stopping the irradiation of the substrate and exposing the surface of the substrate to a camera for a second predetermined period of time, indicated by trace 104. A camera is then used to capture a photoluminescence (PL) signal 106, shown in FIG. 1B, emitted from the surface of the substrate and generated by recombination of photogenerated carriers in the substrate. Optionally or preferably, there is a time delay 108, also of a predetermined duration, between the irradiation and the capture of the PL signal 106 by the camera to insure that characterization or measurement of the PL signal is substantially not effected by light from the light source.

Figure 1B:
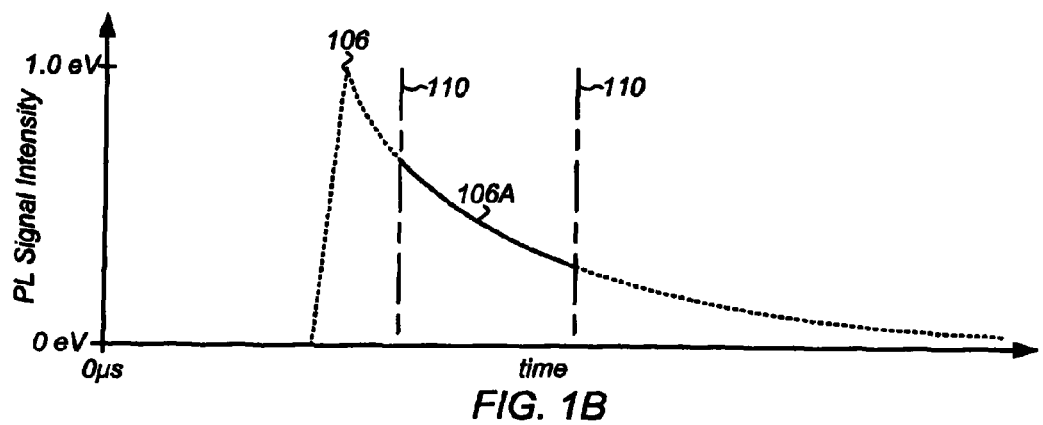
FIG. 1B is a graph illustrating a photoluminescence (PL) signal intensity over time following exposure of substrate to a stimulation light source of FIG. 1A.

It will understood that in the embodiment shown in FIGS. 1A and 1B only a portion of the total PL signal 106, indicated by solid line 106A between dashed lines 110 is captured by the camera. In an alternative embodiment, not shown, substantially the entire PL signal 106 or image can be captured by performing a series of alternating flashes and captures, in which each successive exposure to the camera is preceded by a different or increasing delay 108.

In one exemplary embodiment, for a high lifetime (e.g., 1ms) sample, the first predetermined period of time 102 may be approximately in the range of 10 nanoseconds (ns) to 100 microseconds (μs); delay 108 may be approximately in the range of 0 ns to 5 ms; and the second predetermined period of time 104 may be approximately in the range of 100 ns to 5 ms. Alternatively, traces and delays may have other values depending on the lifetime of sample under measure.

Figure 2:
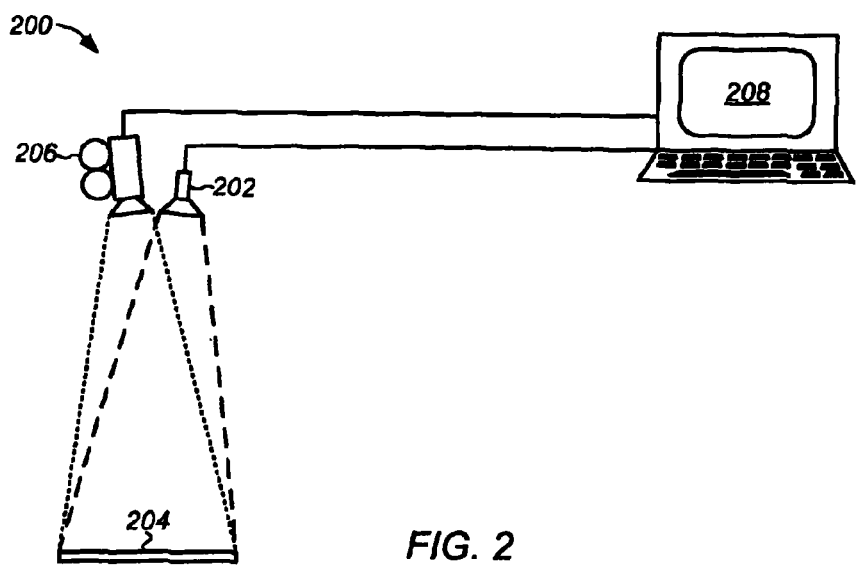
FIG. 2 is a schematic block diagram of a system for measuring transient photoluminescence of a substrate having a high photoluminescence lifetime (LT) according to an embodiment of the present invention.

A schematic block diagram of system for measuring transient photoluminescence of a substrate using the above method is shown in FIG. 2. It will be appreciated by those skilled in the art that by separating in time the exposure of the substrate to irradiation and to the camera, the need for a complex filtering system between the camera and the surface of the substrate is eliminated and the requirements of the light or radiation source simplified.

Referring to FIG. 2, the system 200 generally includes a radiation or light source 202 capable of irradiating the surface of a substrate 204 with photons having at least a predetermined level of energy for a predetermined period of time photogenerate carriers (electron and hole pairs) therein, a camera 206 sensitive to the photoluminescence generated by recombination of the carriers, and a data processor 208 for controlling light source and camera and/or for characterizing the resultant PL signal.

The light source 202 can include any suitable coherent or non-coherent light source capable of producing photons of sufficient energy and at a frequency or wavelength capable of stimulating photogeneration of carriers within the substrate. A significant advantage of the present invention is that enables the use of an inexpensive non-coherent light source, such as a commercially available flash, or a bank of light emitting diodes (LEDs). By a non-coherent light source it is meant a light source capable of producing light or radiation over a broad spectrum of wavelengths. Preferably, the light source is a one-sun standard light source capable of producing light with a spectrum and at an energy level comparable to that of un-enhanced sunlight. A suitable light source for testing silicon substrates, for example, is a commercially available photographic flash.

The camera 206 can include any camera or optical scanner having an array of one or more light-sensitive elements, such a charge-coupled device (CCD), capable of converting a pattern of light into an electrical signal. One suitable camera 206, for example, is an intensified CCD or ICCD camera sensitive to light in the infrared (IR) range. In an ICCD camera a photo-cathode converts incoming photons to electrons, which are then multiplied by a micro-channel plate (MCP). After the MCP a phosphor screen converts the electrons back to photons which are then fiber-optically guided to the CCD to increase the sensitivity. Besides the gain in sensitivity the MCP also enables the ICCD camera to be turned on or gated to capture an image very fast, making it particularly suitable for use with this invention.

The data processor 208 can include any computer, microprocessor or microcontroller capable of controlling the light source 202 and camera 206 and/or for characterizing the resultant PL signal. In a preferred embodiment, the data processor 208 is a general purpose computer such as a personal computer or PC. The data processor 208 may characterized as an exposure control device that can control the sequential exposure of the substrate 204 to the light source 202 and camera 206, for example, by turning on and off or gating the MCP in an ICCD camera, strobing or triggering a flash light source, and/or operating an integral shutter mechanism in the light source, camera or both.

It will be appreciated by those skilled in the art that the single capture method illustrated in FIGS. 1A and 1B and described above, can be easily and inexpensively implemented, and work well for mapping or characterizing substrates having PL signals with a high photoluminescence intensities and/or lifetimes (LT). However, for substrates having PL signals with low photoluminescence intensities and/or low LTs a different approach is desirable. Thus, in another embodiment of the present invention a substrate is sequentially irradiated and viewed with a photoluminescence sensitive camera multiple times to integrate a larger number of photons, providing a series of PL signals that can be analyzed by a data processor to provide the desired information on the test substrate. This embodiment is particularly useful for mapping or characterizing substrates having low LTs. In addition, this approach can enable the use of less sensitive and therefore less expensive cameras to accurately measure the photogeneration rate and the effective lifetime of the carriers in substrates having high or low LTs.

A timing diagram illustrating the multiple exposure and viewing or capture of photoluminescence from the substrate is shown in FIG. 3A, where the exposure to the light source is indicated by traces labeled 302 and the subsequent exposure of the substrate to a camera is indicated by traces labeled 304. FIG. 3B illustrates the resultant PL signal 306 or signals. As in FIG. 1B only a portion of the total PL signal 306 or signals, indicated by solid lines 306A between dashed lines 308, is captured by the camera. Again, as in the method described above, optionally or preferably, there is a time delay of a predetermined duration (not labeled in these figures) between the irradiation and the capture of the PL signal 306 by the camera to insure that characterization or measurement of the PL signal is substantially not effected by light from the light source.

In one exemplary embodiment, for a high lifetime (e.g., 1ms) sample, the exposure time to the light source, traces 302, may be approximately in the range of 100 ns to 100 μs is and the subsequent exposure of the substrate to a camera, traces 304, may be approximately in the range of 10 ns to 5 ms. Alternatively, the exposure times may have other values depending on the lifetime of sample under measure.

Generally, the system 200 shown in FIG. 2 is also suitable for performing the series capture method illustrated in FIGS. 3A and 3B and described above. However, in yet other embodiments systems using mechanical shuttering mechanisms for the camera and/or stimulating light source can also be implemented to perform the series capture method.

A schematic block diagram of one such system for measuring transient photoluminescence is shown in FIGS. 4A and 4B. Referring to FIGS. 4A and 4B, the system 400 generally includes a radiation or light source 402 and a camera 404 similar to those described above, and a data processor 406 for controlling the light source and camera and/or for characterizing the resultant PL signal. In this embodiment the system 400 further includes a movable or rotating mechanical shutter 408, such as a chopper, having one or more apertures 410 therein for controlling exposure of the substrate 412 to the light source and to the camera. A planar top view of an exemplary embodiment of the mechanical shutter 408 showing the apertures 410 is illustrated in FIG. 4B.

It will be appreciated by those skilled in the art that the duration or duty cycle with which the surface or the substrate 412 is exposed to the light source 402 (and to viewing by the camera 404) can be controlled by controlling the speed with which the mechanical shutter 408 is moved or rotated. For example, a substrate 412 be tested and having an LT of ~10 μs would require a duty cycle of ~100,000 Hz and the mechanical shutter 408 should be rotated at a speed of about 10,000 rpm. Thus, in one version of this embodiment the data processor 406 can also be used to control and adjust the speed of the mechanical shutter 408 as needed to test substrates 412 having different LTs. In such an embodiment, the mechanical shutter 408 and the data processor 406 may operate in combination as an exposure control device.

Figure 5:
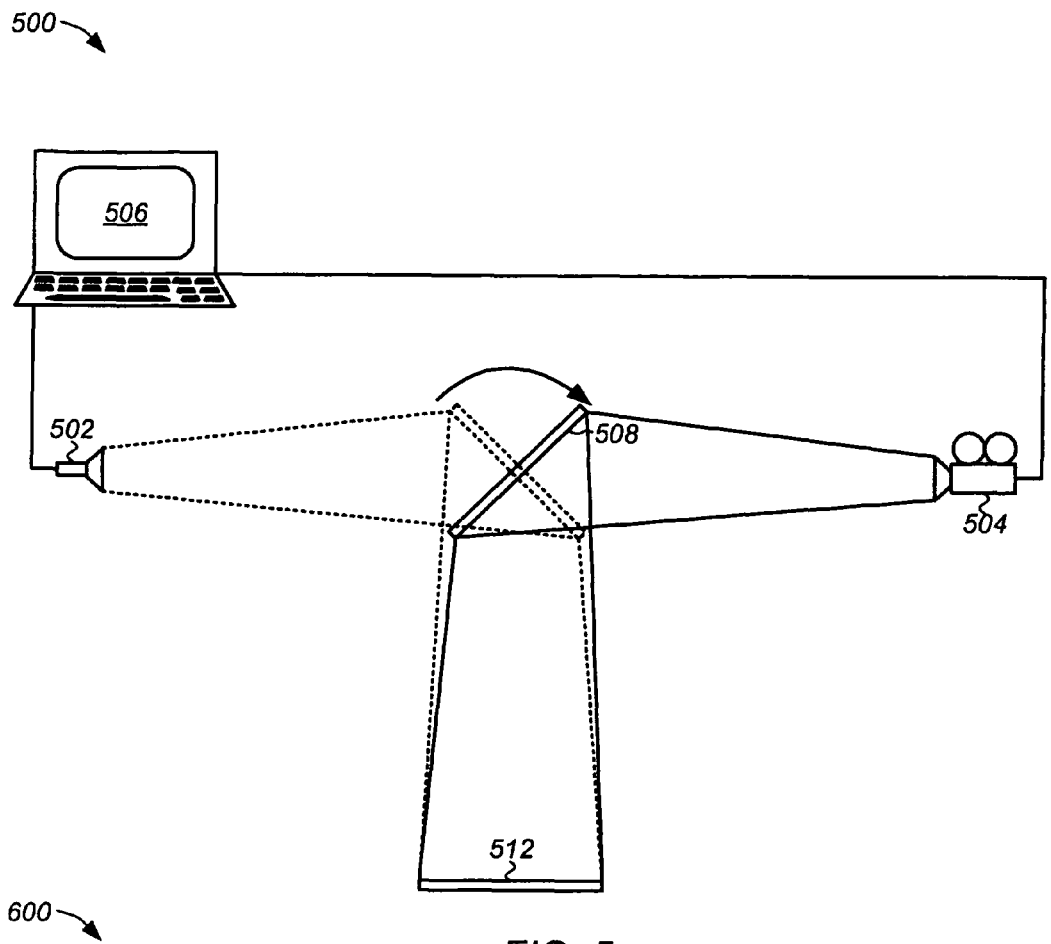
FIG. 5 is a schematic block diagram of a system for measuring transient photoluminescence of a substrate having a low photoluminescence LT according to another embodiment of the present invention.

A schematic block diagram of a system for measuring transient photoluminescence of a substrate having a low LT using the above method according to another embodiment is shown in FIG. 5. Referring to FIG. 5, the system 500 generally includes a radiation or light source 502 and a camera 504 similar to those described above, and a data processor 506 for controlling the light source and camera and/or for characterizing the resultant PL signal. In this embodiment the system 500 further includes a movable or rotating mirror 508, having one or more reflective surfaces for controlling exposure of the substrate 510 to the light source and to the camera. Although shown as 2-sided flat or planar mirror, it will be appreciated that the mirror can alternatively include a cylindrical shape having any number of reflective surfaces. It will further be appreciated that as with the embodiments described with reference to FIGS. 4A and 4B, the data processor 506 can also be used to control and adjust the speed of the mirror 508 as needed to test substrates 510 having different LTs. In such an embodiment, the mirror 508 and the data processor 506 may operate in combination as an exposure control device.

Figure 6:
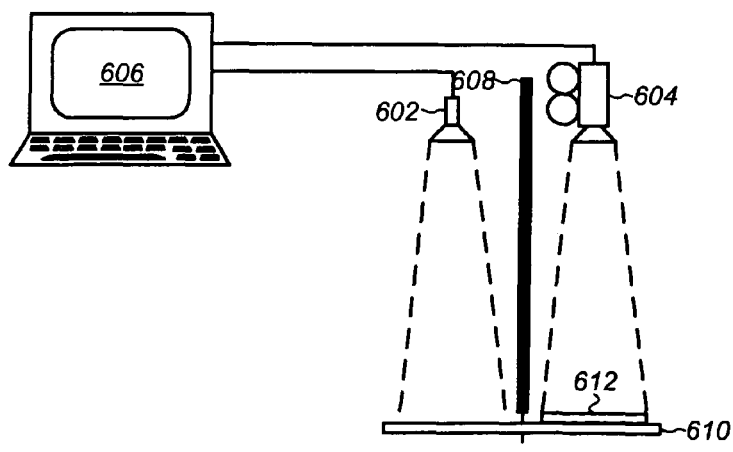
FIG. 6 is a schematic block diagram of a system for measuring transient photoluminescence of a substrate having a low photoluminescence LT according to yet another embodiment of the present invention.

A schematic block diagram of a system for measuring transient photoluminescence of a substrate using the above method according to another embodiment is shown in FIG. 6. Referring to FIG. 6, the system 600 generally includes a radiation or light source 602 and a camera 604 similar to those described above, and a data processor 606 for controlling the light source and camera and/or for characterizing the resultant PL signal. In this embodiment the system 600 further includes a light barrier 608 between the light source 602 and camera 604 and a movable platen or turntable 610 on which a substrate 612 is held. As the turntable 610 is rotated the substrate 612 is alternately exposed to the light source 602 and camera 604. As with the embodiments described above, the data processor 606 can also be used to control and adjust the speed of the turntable 610 as needed to test multiple substrates 612 and/or substrates having different LTs. In such an embodiment, the turntable 610 and the data processor 606 may operate in combination as an exposure control device.

In another aspect of the present invention, illustrated in FIGS. 7A through 7C, a substrate or a number of pixels thereon can be repeatedly flashed followed by exposure to the camera at a different time following each flash to determine the decay of the photoluminescence signal, thereby enabling an effective lifetime to be extracted or calculated for the substrate or a number of pixels. A timing diagram illustrating this multiple exposure and viewing or capture of photoluminescence from the substrate is shown in illustrated in FIGS. 7A and 7B, where the exposure to the light source is indicated by traces labeled 702 and the subsequent exposure of the substrate to a camera is indicated by traces labeled 704, and the resultant PL signal 706 is illustrated in FIG. 7B. Referring to FIG. 7B, in the embodiment shown it is seen that a different portion of the PL signal 706, illustrated by the area between the dashed lines 708A through 708D, is captured following each flash. Referring to FIG. 7C, it is seen that these different portions can then be combined to provide the decay of the photoluminescence signal, and enable calculation of the effective lifetime. It will be understood that this determination of photoluminescence signal decay and calculation of the effective lifetime is not possible with conventional steady state testing systems. It will further be appreciated that this embodiment also enables calibrated, spatially resolved lifetime measurements across the surface of the substrate.

The advantages of the photoluminescence mapping system and method for fabricating solar cells of the present invention over previous or conventional systems and methods include reduced cost and complexity for the system and reduced complexity and testing time for the method. The system and method of the invention further provide increased sensitivity and testing accuracy for all substrates, including those having low LTs, while enabling use of less sensitive and less expensive cameras.

The foregoing description of specific embodiments and examples of the invention have been presented for the purpose of illustration and description, and although the invention has been described and illustrated by certain of the preceding examples, it is not to be construed as being limited thereby. They are not intended to be exhaustive or to limit the invention to the precise forms disclosed, and many modifications, improvements and variations within the scope of the invention are possible in light of the above teaching. It is intended that the scope of the invention encompass the generic area as herein disclosed, and by the claims appended hereto and their equivalents. The scope of the present invention is defined by the claims, which includes known equivalents and unforeseeable equivalents at the time of filing of this application.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method of characterizing photoluminescence of a semiconductor substrate used in fabrication of a solar cell, the method comprising:
    irradiating a surface of the substrate with radiation having a predetermined energy for a first predetermined finite period of time to photogenerate carriers therein;
    stopping the irradiation of the substrate at the end of the first predetermined finite period of time;
    exposing the surface of the substrate to a camera for a second predetermined finite period of time, the start of the second predetermined finite period of time non-overlapping with the first predetermined finite period of time and delayed from the end of the first predetermined finite period of time by a third predetermined finite period of time, wherein the substrate is not irradiated during the second and third predetermined finite periods of time; and capturing with the camera a photoluminescence (PL) signal emitted from the surface of the substrate and generated by recombination of the carriers therein.

2. A method according to claim 1, further comprising measuring a peak intensity of the PL signal and the PL signal's decay rate over the second predetermined finite period of time.

3. A method according to claim 2, further comprising mapping the PL signal over the surface of the substrate.

4. A method according to claim 1, wherein irradiating a surface of the substrate and capturing the PL signal with the camera comprises a number of repeated sequential exposures of the surface of the substrate to the radiation and to the camera to increase a sensitivity of the method to low level PL signals.

5. A method according to claim 1, wherein irradiating the surface, stopping the irradiation and exposing the surface of the substrate to the camera are controlled using a data processor.

6. A method according to claim 1, wherein irradiating the surface, stopping the irradiation and exposing the surface of the substrate to the camera are controlled using a mechanical shutter.

7. A method according to claim 1, wherein the irradiating a surface of the substrate and capturing the PL signal with the camera comprises a number of repeated sequential exposures of the surface of the substrate to the radiation and to the camera, and wherein there is a different finite time delay following each irradiating step to determine a decay of the PL signal.

8. A system for measuring photoluminescence of a semiconductor substrate used in fabrication of a solar cell, the system comprising:
 a radiation source for irradiating a surface of the substrate with radiation having a predetermined energy to photo-generate carriers therein;
 a camera for capturing a photoluminescence (PL) signal emitted from the surface of the substrate and generated by recombination of the carriers therein; and
 an exposure control device to control exposure of the surface of the substrate to the radiation source and to the camera to provide sequential exposure of the surface to the radiation source for a first predetermined finite period of time followed by exposure of the surface to the camera for a second predetermined finite period of time, the second predetermined finite period of time non-overlapping with the first predetermined finite period of time and delayed from the first predetermined finite period of time by a third predetermined finite period of time, wherein the substrate is not irradiated during the second and third predetermined finite periods of time.

9. A system according to claim 8, wherein the exposure control device comprises at least one of a data processor to control the radiation source and a camera.

10. A system according to claim 9, wherein the data processor is configured to control at least one of the radiation source and the camera by turning on and off the camera, strobing or triggering a flash light source, or operating an integral shutter mechanism in the light source, camera or both.

11. A system according to claim 9, wherein the camera comprises an intensified charge coupled device (ICCD) camera, and wherein the data processor is configured to control the camera by turning on and off or gating a micro-channel plate (MCP) in the ICCD camera.

12. A system according to claim 8, wherein the exposure control device comprises a mechanical shutter to expose only one of the radiation source or the camera to the surface of the substrate at a time.

13. A system according to claim 12, wherein the exposure control device comprises a data processor to control the mechanical shutter.

14. A system according to claim 12, wherein the mechanical shutter comprises a chopper.

15. A system according to claim 8, wherein the exposure control device comprises a rotating mirror to expose only one of the radiation source or the camera to the surface of the substrate at a time.

16. A system according to claim 15, wherein the exposure control device comprises a data processor to control the rotation of the mirror.

17. A system according to claim 8, wherein the exposure control device comprises a light barrier separating the radiation source and the camera, and a movable or rotating platen to expose only one of the radiation source or the camera to the surface of the substrate at a time.

18. A system according to claim 17, wherein the exposure control device further comprises a data processor to control the position of the platen.

19. A system for measuring photoluminescence of a semiconductor substrate used in fabrication of a solar cell, the system comprising:
 a radiation source for irradiating a surface of the substrate with radiation having a predetermined energy to photo-generate carriers therein;
 a camera for capturing a photoluminescence (PL) signal emitted from the surface of the substrate and generated by recombination of the carriers therein; and
 an exposure control device to control exposure of the surface of the substrate to the radiation source and to the camera to provide sequential exposure of the surface to the radiation source for a first predetermined period of time followed by exposure of the surface to the camera for a second predetermined period of time, wherein the exposure control device comprises a rotating mirror to expose only one of the radiation source or the camera to the surface of the substrate at a time.

20. A system according to claim 19, wherein the exposure control device comprises a data processor to control the rotation of the mirror.

* * * * *